US00PP26492P2

(12) United States Plant Patent
Heuger

(10) Patent No.: US PP26,492 P2
(45) Date of Patent: Mar. 8, 2016

(54) ***HELLEBORUS* PLANT NAMED 'COSEH 3010'**

(50) Latin Name: *Helleborus niger*
Varietal Denomination: COSEH 3010

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 184 days.

(21) Appl. No.: 13/999,076

(22) Filed: Jan. 10, 2014

(51) Int. Cl.
*A01H 5/02* (2006.01)

(52) U.S. Cl.
USPC ..... Plt./439

(58) Field of Classification Search
USPC ..... Plt./439
See application file for complete search history.

*Primary Examiner* — Anne Grunberg
(74) *Attorney, Agent, or Firm* — C. A. Whealy

(57) ABSTRACT

A new and distinct cultivar of *Helleborus* plant named 'COSEH 3010', characterized by its upright and mounding plant habit; uniform and freely flowering habit; dark green-colored leaves; freely and early flowering habit; single white and light yellow green-colored flowers; and good garden performance.

2 Drawing Sheets

Botanical designation: *Helleborus niger.*
Cultivar denomination: 'COSEH 3010'.

BACKGROUND OF THE INVENTION

The present invention relates to a new and distinct cultivar of *Helleborus* plant, botanically known as *Helleborus niger* and hereinafter referred to by the name 'COSEH 3010'.

The new *Helleborus* plant is a product of a planned breeding program conducted by the Inventor in Glandorf, Germany. The objective of the breeding program was to create new uniform *Helleborus* plants with unique and attractive leaf and flower forms and coloration and resistance to pests common to *Helleborus* plants.

The new *Helleborus* plant originated from a cross-pollination conducted by the Inventor in Glandorf, Germany in December, 2008 of two unnamed proprietary seedling selections of *Helleborus niger*, not patented. The new *Helleborus* plant was discovered and selected by the Inventor as a single flowering plant from within the progeny of the stated cross-pollination grown in a controlled greenhouse environment in Glandorf, Germany in November, 2010.

Asexual reproduction of the new *Helleborus* plant by divisions in a controlled environment in Glandorf, Germany since February, 2011 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 3010'. These characteristics in combination distinguish 'COSEH 3010' as a new and distinct *Helleborus* plant:

1. Upright and mounding plant habit.
2. Uniform and freely flowering habit.
3. Dark green-colored leaves.
4. Freely and early flowering habit.
5. Single white and light yellow green-colored flowers.
6. Good garden performance.

Compared to plants of the parent selections, plants of the new *Helleborus* are more uniformly mounded and are more freely flowering.

Plants of the new *Helleborus* can be compared to plants of *Helleborus niger* 'COSEH 230', disclosed in U.S. Plant Pat. No. 21,242. In side-by-side comparisons conducted in Glandorf, Germany, plants of the new *Helleborus* differed primarily from plants of 'COSEH 230' in the following characteristics:

1. Flowers of plants of the new *Helleborus* were single in form whereas flowers of plants of 'COSEH 230' were semi-double in form.
2. Plants of the new *Helleborus* flowered earlier than plants of 'COSEH 230'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 3010' grown in a container.

The photograph on the second sheet is a close-up view of a typical flower of 'COSEH 3010'.

DETAILED BOTANICAL DESCRIPTION

The aforementioned photographs and following observations, measurements and values describe plants grown during the autumn in 13-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger* 'COSEH 3010'.

Parentage:

*Female, or seed, parent*.—Unnamed proprietary seedling selection of *Helleborus niger*, not patented.

*Male, or pollen, parent*.—Unnamed proprietary seedling selection of *Helleborus niger*, not patented.

Propagation:

*Type*.—By tissue culture.

*Time to initiate roots, winter*.—About two months at temperatures about 12° C.

*Time to produce a rooted young plant, winter*.—About six months at temperatures ranging from 4° C. to 15° C.

*Root description*.—Thick to thin, fleshy; white to brown in color.

*Rooting habit*.—Sparse.

Plant description:

*Plant and growth habit*.—Herbaceous perennial; upright and mounding plant habit with flowers held just above the foliar plane; plant shape is roughly globular; moderately vigorous growth habit.

*Plant height, soil level to top of foliar plane*.—About 18.5 cm.

*Plant height, soil level to top of flowers*.—About 22.5 cm.

*Plant diameter* (*area of spread*).—About 32.2 cm.

Leaf description:

*Arrangement*.—Leaves arranged in a basal rosette; leaves palmately compound with seven leaflets per leaf.

*Leaf length*.—About 10.2 cm.

*Leaf width*.—About 12.4 cm.

*Leaflet length*.—About 7.2 cm.

*Leaflet width*.—About 3.3 cm.

*Leaf shape*.—Palmate; orbicular to reniform in outline.

*Leaflet shape*.—Obovate to narrowly obovate.

*Leaflet apex*.—Acute to bluntly acute.

*Leaflet base*.—Attenuate.

*Leaflet margin*.—Serrate.

*Leaflet texture, upper and lower surfaces*.—Smooth, glabrous; leathery.

*Leaflet luster, upper and lower surfaces*.—Moderately glossy.

*Leaflet venation pattern*.—Pinnate.

*Leaflet color*.—Developing leaves, upper surface: Close to 137D and 138A. Developing leaves, lower surface: Close to 143C. Fully developed leaves, upper surface: Between 139A and 147A; venation, close to 143B. Fully developed leaves, lower surface: Close to 147B; venation, close to 145A.

*Petioles*.—Length: About 12.4 cm. Diameter: About 5 mm. Texture, upper and lower surfaces: Smooth, glabrous. Color, upper and lower surfaces: Close to 144B to 144C moderately speckled with close to 183A; towards the base, densely speckled with close to 187C.

Flower description:

*Flower shape and habit*.—Single rotate flowers arranged singly or in pairs; freely and uniform flowering habit with about 30 flowers developing per plant; flowers facing mostly outwardly.

*Fragrance*.—None detected.

*Natural flowering season*.—Plants begin flowering about ten months after planting; plants flower from autumn into winter in Germany.

*Flower longevity on the plant*.—About ten days; flowers not persistent.

*Flower buds*.—Length: About 2.2 cm. Diameter: About 1 cm. Shape: Ovate. Color: Close to NN155A; towards the base, tinged with close to 157D.

*Flower diameter*.—About 8 cm.

*Flower depth* (*height*).—About 2.1 cm.

*Petals*.—Transformed into nectaries.

*Sepals*.—Quantity and arrangement: Five, arranged in a single whorl. Length: About 4.3 cm. Width: About 3.6 cm. Shape: Broadly ovate. Apex: Obtuse. Base: Broadly cuneate. Margin: Entire. Texture, upper and lower surfaces: Smooth, glabrous. Color: When opening, upper surface: Close to NN155C; towards the base, close to 145B. When opening, lower surface: Close to NN155D; towards the base, close to 145B. Fully opened, upper surface: Close to 155C tinged with close to 150D; towards the base, close to 145A. Fully opened, lower surface: Close to 155C tinged with close to 150D; towards the apex, slightly tinged with close to N170D; towards the base, close to 145A.

*Peduncles*.—Length: About 9.4 cm. Diameter: About 5.5 mm. Aspect: About 15° from vertical. Strength: Moderately strong. Texture: Smooth, glabrous. Color: Close to 144C heavily speckled with close to 178A; towards the base, speckling is closer to 184B to 184C.

*Pedicels*.—Length: About 10.4 cm. Diameter: About 3.5 mm. Aspect: About 15° from peduncle axis. Strength: Moderately strong. Texture: Smooth, glabrous. Color: Close to 144C heavily speckled with close to 178A; towards the base, speckling is closer to 184B to 184C.

*Reproductive organs*.—Stamens: Quantity per flower: About 120. Filament length: About 1.6 cm. Filament color: Close to NN155D. Anther shape: Reniform; basifixed. Anther length: About 2 mm. Anther color: Close to 3B. Pollen amount: Moderate. Pollen color: Close to 4C to 4D. Pistils: Quantity per flower: About five to seven. Pistil length: About 8 mm. Stigma shape: Club-shaped. Stigma color: Close to 155A. Style length: About 7.5 mm. Style color: Close to NN155B. Ovary color: Between 145D and 150C. Nectaries (transformed petals): Quantity per flower: About 14. Length: About 8 mm. Diameter: About 2 mm. Shape: Tubular, flattened. Color, immature, inner and outer surfaces: Close to N144C. Color, mature, inner and outer surfaces: Close to N144C;

towards the apex, close to N144B; with development, color becoming closer to 151A and towards the apex, close to 14B.

*Seeds and fruits*.—Seed and fruit development have not been observed on plants of the new *Helleborus*.

Garden performance: Plants of the new *Helleborus* have been observed to have good garden performance and to tolerate rain, wind and high temperatures about 35° C. and to be hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 3010' as illustrated and described.

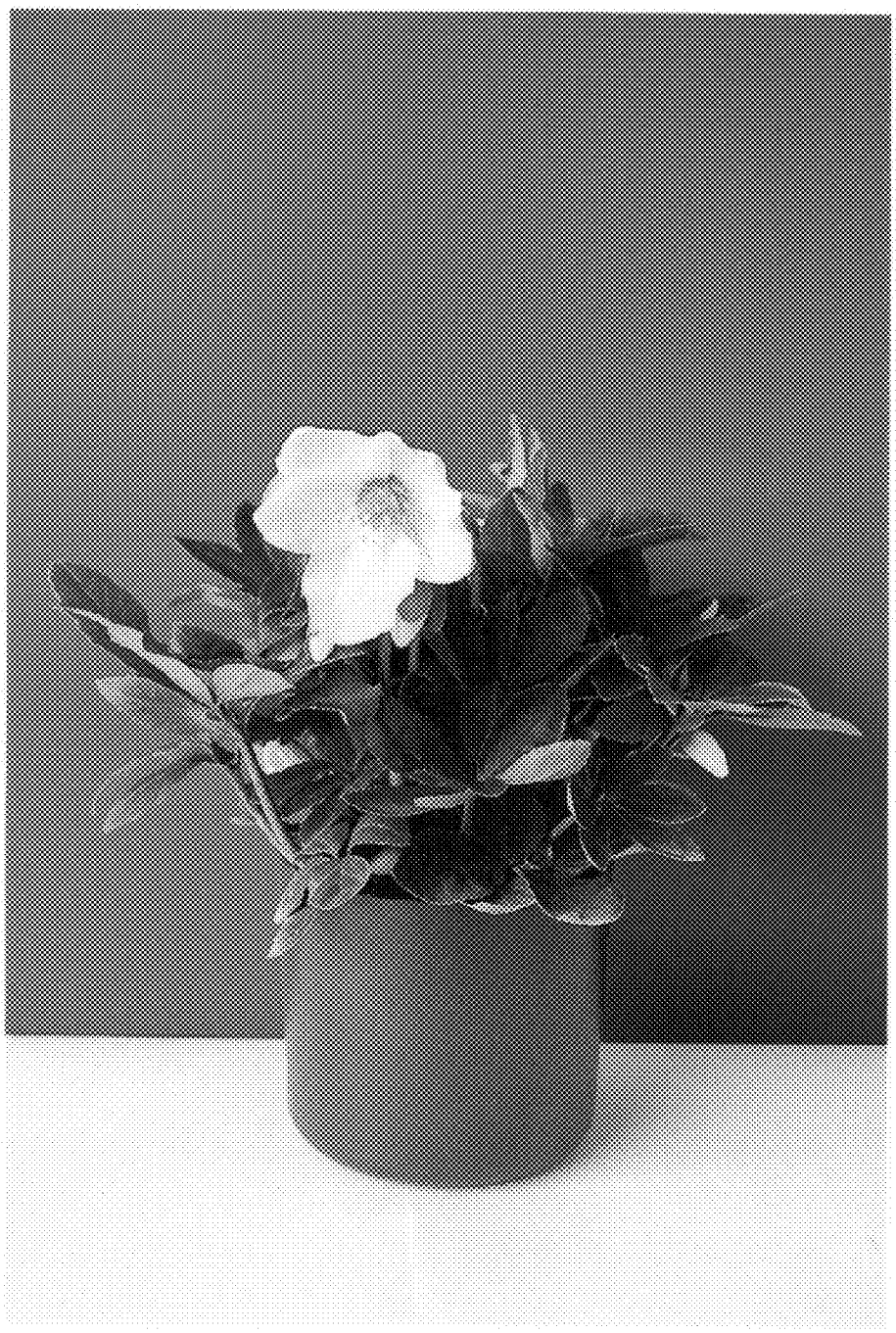

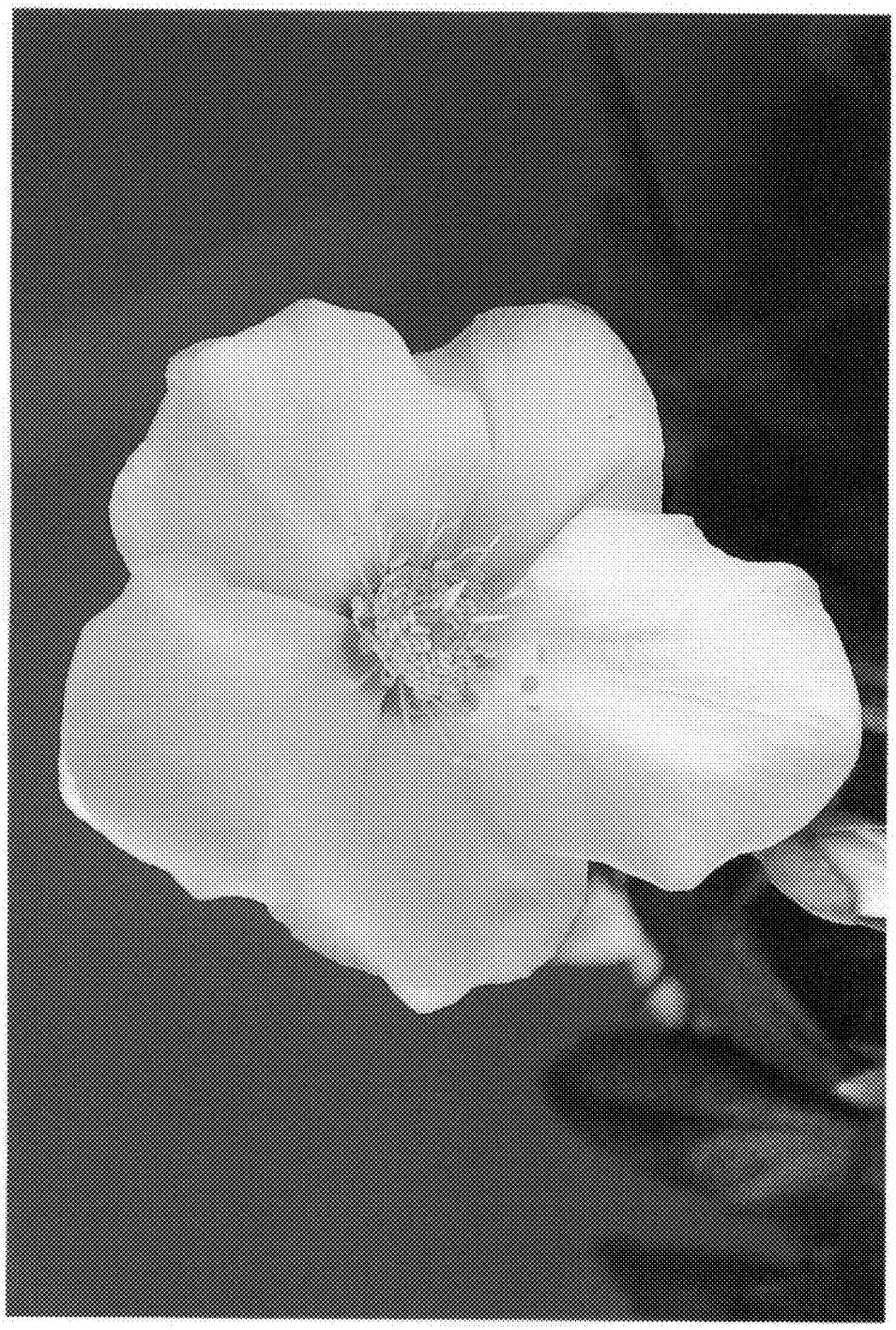

* * * * *